United States Patent
Chobotov

Patent Number: 6,132,457
Date of Patent: *Oct. 17, 2000

[54] ENDOVASCULAR GRAFT HAVING LONGITUDINALLY DISPLACEABLE SECTIONS

[75] Inventor: Michael V. Chobotov, Santa Rosa, Calif.

[73] Assignee: Triad Vascular Systems, Inc., Santa Rosa, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/177,295

[22] Filed: Oct. 22, 1998

Related U.S. Application Data

[60] Provisional application No. 60/062,639, Oct. 22, 1997.

[51] Int. Cl.$^7$ .............................. A61F 2/06; A61F 2/04; A61M 29/00
[52] U.S. Cl. .................................. 623/1; 623/1; 623/12; 606/195; 606/198
[58] Field of Search .................... 623/1, 12; 606/198, 606/195

[56] References Cited

U.S. PATENT DOCUMENTS

| | | | |
|---|---|---|---|
| 5,064,435 | 11/1991 | Porter | 623/12 |
| 5,549,662 | 8/1996 | Fordenbacher | 623/1 |
| 5,725,549 | 3/1998 | Lam | 606/198 |
| 5,782,904 | 7/1998 | White et al. | 623/1 |
| 5,797,951 | 8/1998 | Mueller | 606/198 |
| 5,833,707 | 11/1998 | McIntyre et al. | 606/198 |

Primary Examiner—Michael J. Milano
Assistant Examiner—Hieu Phan
Attorney, Agent, or Firm—Heller Ehrman White & McAuliffe LLP

[57] ABSTRACT

An endovascular graft having at least two barrier sections coupled to form a substantially tubular member. The barrier sections are coupled or connected to each other so as to allow relative axial displacement of the sections. The axial displacement of the barrier sections of the graft allows for a reduced profile and increased flexibility during delivery of the device to a desired site for deployment. The device may be delivered percutaneously or intraoperatively.

10 Claims, 6 Drawing Sheets

ENDOVASCULAR GRAFT HAVING LONGITUDINALLY DISPLACEABLE SECTIONS

RELATED APPLICATIONS

This application is a continuation-in-part of Provisional application Ser. No. 60/062,639, filed Oct. 22, 1997. Priority is hereby claimed to Provisional application Ser. No. 60/062, 639, which also incorporated by reference in its entirety herein.

BACKGROUND OF THE INVENTION

The present invention relates to a system and method for the treatment of disorders of the vasculature. More specifically, a system and method for treatment of thoracic or abdominal aortic aneurysm and the like, which is a condition manifested by expansion and weakening of the aorta. Such conditions require intervention due to the severity of the sequelae, which frequently is death. Prior methods of treating aneurysms have consisted of invasive surgical methods with graft placement within the affected vessel as a reinforcing member of the artery. However, such a procedure requires a surgical cut down to access the vessel, which in turn can result in a catastrophic rupture of the aneurysm due to the decreased external pressure from the surrounding organs and tissues, which are moved during the procedure to gain access to the vessel. Accordingly, surgical procedures have a high mortality rate due to the possibility of the rupture discussed above in addition to other factors. Other factors can include poor physical condition of the patient due to blood loss, anuria, and low blood pressure associated with the aortic abdominal aneurysm. An example of a surgical procedure is described in a book entitled *Surgical Treatment of Aortic Aneurysms* by Denton A. Cooley, M.D., published in 1986 by W.B. Saunders Company.

Due to the inherent risks and complexities of surgical procedures, various attempts have been made in the development of alternative methods for deployment of grafts within aortic aneurysms. One such method is the non-invasive technique of percutaneous delivery by a catheter-based system. Such a method is described in Lawrence, Jr. et al. in "Percutaneous endovascular graft: experimental evaluation", *Radiology* (May 1987). Lawrence described therein the use of a Gianturco stent as disclosed in U.S. Pat. No. 4,580,568. The stent is used to position a Dacron fabric graft within the vessel. The Dacron graft is compressed within the catheter and then deployed within the vessel to be treated. A similar procedure has also been described by Mirich et al in "Percutaneously placed endovascular grafts for aortic aneurysms: feasibility study," *Radiology* (March 1989). Mirich describes therein a self-expanding metallic structure covered by a nylon fabric, with said structure being anchored by barbs at the proximal and distal ends.

One of the primary deficiencies of the existing percutaneous devices and methods has been that the grafts and the delivery catheters used to deliver the grafts are relatively large in profile, often up to 24 French and greater, and stiff in bending. The large profile and bending stiffness makes delivery through the irregular and tortuous arteries of diseased vessels difficult and risky. In particular, the iliac arteries are often too narrow or irregular for the passage of a percutaneous device. Because of this, non-invasive percutaneous graft delivery for treatment of aortic aneurysm is not available to many patients who would benefit from it.

While the above methods have shown some promise with regard to treating thoracic and abdominal aortic aneurysms with non-invasive methods, there remains a need for an endovascular graft system which can be deployed percutaneously in a small diameter flexible catheter system. The present invention satisfies these and other needs.

SUMMARY OF THE INVENTION

The present invention is directed generally to an endovascular graft for vascular treatment and a method for deploying the graft within a patient's body. More specifically, the invention is directed to an endovascular graft which has at least two barrier sections which are formable into a substantially tubular structure. At least one of the barrier sections has a first and second lateral edge which are slidably connected or coupled to an adjacent barrier section or sections to allow axial movement or displacement of the at least one barrier section relative to the adjacent barrier section or sections. This configuration allows the endovascular graft to be effectively stretched longitudinally by displacing barrier sections relative to one another so that the volume of the graft can be spread out over a greater longitudinal length which in turn decreases the transverse profile and increases the flexibility of the graft. An endovascular graft in such a stretched or elongated state may be readily loaded into a delivery catheter having a relatively small outer diameter and high flexibility for delivery to a desired site within a patient's body.

The barrier sections of an endovascular graft having features of the invention may have a distal support member and a proximal support member which are connected or secured to the first lateral edge and second lateral edge so as to form a frame which surrounds an opening. The opening surrounded by the frame may be covered by a thin membrane which can prevent or impede the passage of blood or other bodily fluids therethrough. Preferably, the thin membrane is made of a polymer mesh or membrane such as TFE, ePTFE, Dacron® or Nylon®.

The frame as made up of the distal support member, proximal support member, first lateral edge or second lateral edge may be made of a variety of materials including polymers such as PVC, TFE, polycarbonate, composite materials including polymers and high strength fiber compositions and the like. The frame may also be made wholly or partially of metals such as stainless steel or pseudoelastic alloys such as NiTi or the like.

The lateral edge of a barrier member may have a female longitudinal member or male longitudinal member disposed thereon and secured to the barrier member. The longitudinal members are preferably secured at their proximal or distal ends to the proximal and distal support members. The female longitudinal member preferably has a channel that extends longitudinally from the proximal end of the member to the distal end of the member. The channel is typically configured to slidingly accept a channel engager or engaging portion of a male longitudinal member. The channel and channel engager are preferably shaped so as to allow relative longitudinal movement or displacement between the male and female longitudinal members, but prevent or restrict relative circumferential movement between the male and female longitudinal members. It is also desirable for the shape of the channel and channel engager to prevent or restrict relative rotational movement between the male and female longitudinal members. This arrangement allows the barrier sections to be coupled or connected circumferentially lateral edge to lateral edge to form a cylindrical or tubular structure inside a patient's blood vessel which resists external compressive forces and internal expansive forces due to the coupling which limits or restricts relative circumferential movement between the male and female longitudinal members and therefor between adjacent barrier members slidingly connected or coupled by the longitudinal members.

In another embodiment of a graft having features of the invention, the barrier members may be coupled or connected lateral edge to lateral edge at all junctions except one which is subsequently joined during deployment in the patient's body. This allows the graft to assume a very low profile and decreased stiffness in an elongated or stretched state because it is not doubled on itself inside the delivery catheter. The uncoupled male and female longitudinal member can be slidingly coupled or connected within the patient's body with a closure wire, string, or other tensile member which passes through the uncoupled members and can be pulled on and shortened to bring the two members together.

Preferably, the relative longitudinal movement between coupled male and female longitudinal members is limited by one or more stops. The stops are typically located in the channel or on the channel engager or in both locations and are configured to prevent the male and female longitudinal members from disengaging completely when the graft is being elongated for loading in a delivery catheter. The stops may consist of a rise or boss on either the male or female longitudinal member or the channel or channel engager thereof. The stops may also have dimples or detents arranged to engage the rise or boss in order for the male and female longitudinal members to lock into an axially elongated or compressed state or any position therebetween. Preferably one of the stops on the female longitudinal member consists of an end plate on either end of the channel which blocks the channel at that end and prevents a channel engager from extending beyond it.

In addition, in one embodiment of a graft having features of the invention, an elastic member, such as a spring or the like, may be secured to a male longitudinal member and a female longitudinal member to provide a restoring force which resists relative axial movement between the members and causes self deployment upon release of the graft from a stretched or elongated state.

A method for using or delivering an endovascular graft having features of the invention would typically involve stretching an endovascular graft having axially moveable or displaceable barrier sections so as to cause displacement between those sections and increase the overall length of the graft and decrease the cross section. The stretched or elongated graft is then loaded into an appropriate delivery catheter. An appropriate delivery catheter may consist of an elongated tubular member of polymer material with an inside diameter suited for housing the graft in an elongated or stretched state. The delivery catheter and graft are positioned in a desired location within a patient's body, preferably with the distal end of the delivery catheter adjacent the desired site. The graft is then deployed from the distal end of the delivery catheter by a push rod or withdrawal of an outer jacket of the delivery catheter relative to the elongated graft. A push rod can be used to eject the elongated graft from the distal end of the delivery catheter one or two barrier sections at a time, preferably from the distal end of the graft so as to prevent expansion of the graft within the delivery catheter inner lumen during the process.

The ability of the barrier members to slide longitudinally relative to each other allows the mass of the graft to be spread over a greater longitudinal or axial length which decreases the cross section at any given point along the length of the graft and makes the graft more flexible and able to be loaded into a smaller diameter delivery catheter.

These and other advantages of the invention will become more apparent from the following detailed description of the invention when taken in conjunction with the accompanying exemplary drawings.

DETAILED DESCRIPTION OF THE INVENTION

Figure 1:
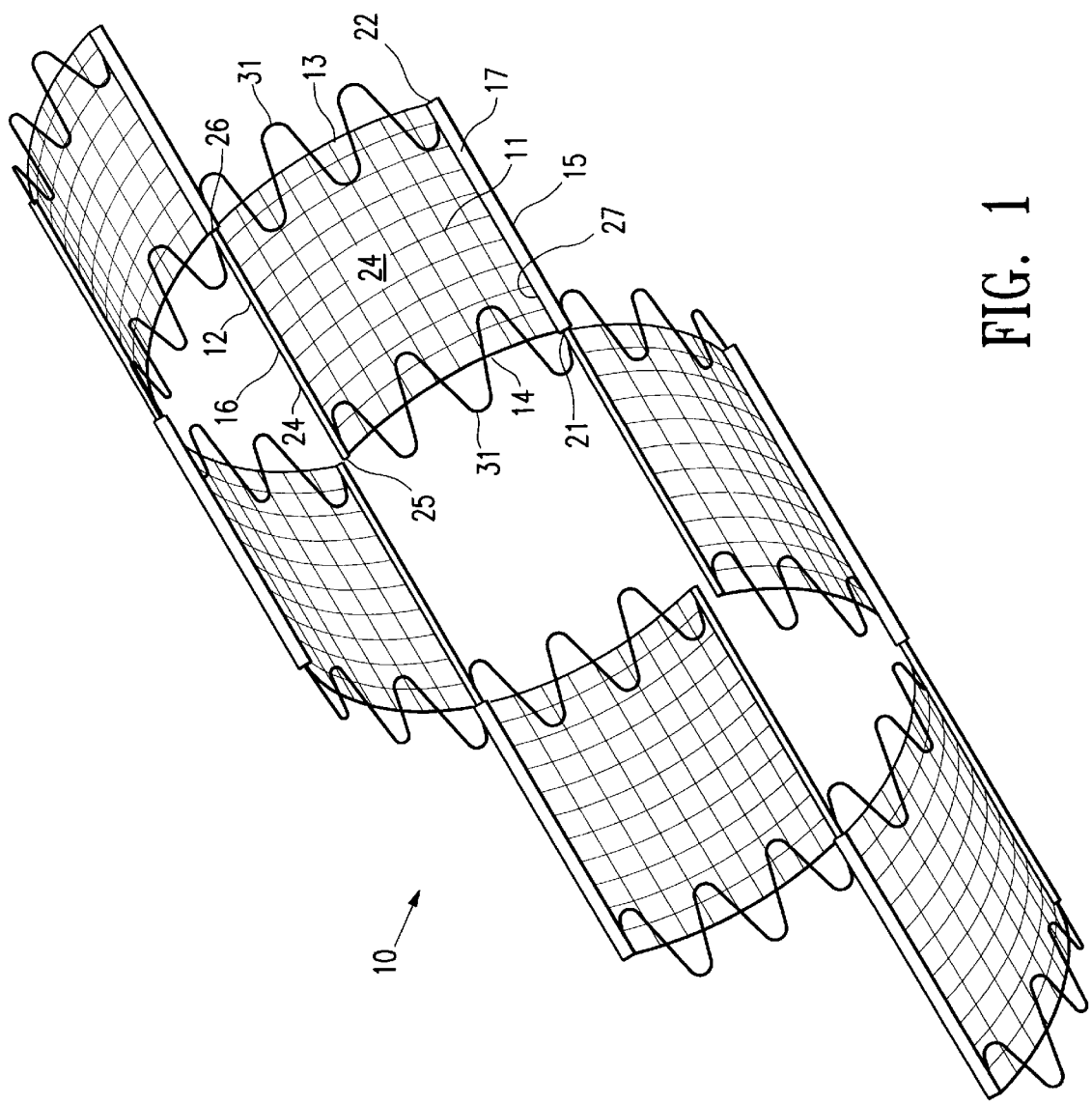
FIG. 1 shows a perspective view of an endovascular graft having features of the invention.

FIG. 1 shows a perspective view of an endovascular graft 10 having features of the invention in a stretched or extended state. The endovascular graft 10 has barrier sections 11 formed by a frame 12 having a distal support member 13, a proximal support member 14, a first lateral edge 15 and a second lateral edge 16. A female longitudinal member 17 having a proximal end 21 and distal end 22 is disposed on the first lateral edge 15 and a male longitudinal member 24 having proximal end 25 and a distal end 26 is disposed on the second lateral edge 16. The distal support member 13, proximal support member 14, female longitudinal member 17 and male longitudinal member 24 define a frame 12 which surrounds an opening 27 which is covered by a thin membrane 28. The thin membrane 28 can be made from a variety of suitable materials including polyethylene, PET, polyurethane, TFE, PTFE, ePTFE, PVC and the like. The thickness of the thin membrane can be from about 0.1 to about 0.5 mm, preferably about 0.15 to about 0.25 mm.

An optional stent member 31 is disposed between the proximal end 21 of the female longitudinal member 17 and the proximal end 25 of the male longitudinal member 24, and the distal end 22 of the female longitudinal member 17 and the distal end 26 of the male longitudinal member 24. The stent members 31 provide additional support for the frame 12. The stent members 31 can be made from a variety of high strength or pseudoelastic materials including MP35N, stainless steel, NiTi alloys, fiber composites and the like. The material from which the stent members 31 are made can have a diameter or cross sectional dimension of about 0.1 to about 1.5 mm, preferably about 0.25 to about 1 mm. The distal and proximal support members 13 and 14 can be similarly constructed.

In order to facilitate visualization of the graft 10 under flouroscopy or similar imaging techniques, radiopaque materials such as gold, platinum, tantalum, bismuth, barium sulfate and the like can be incorporated into or secured to any portion of the barrier section 11, including the frame 12 and thin membrane 28.

Figure 2:
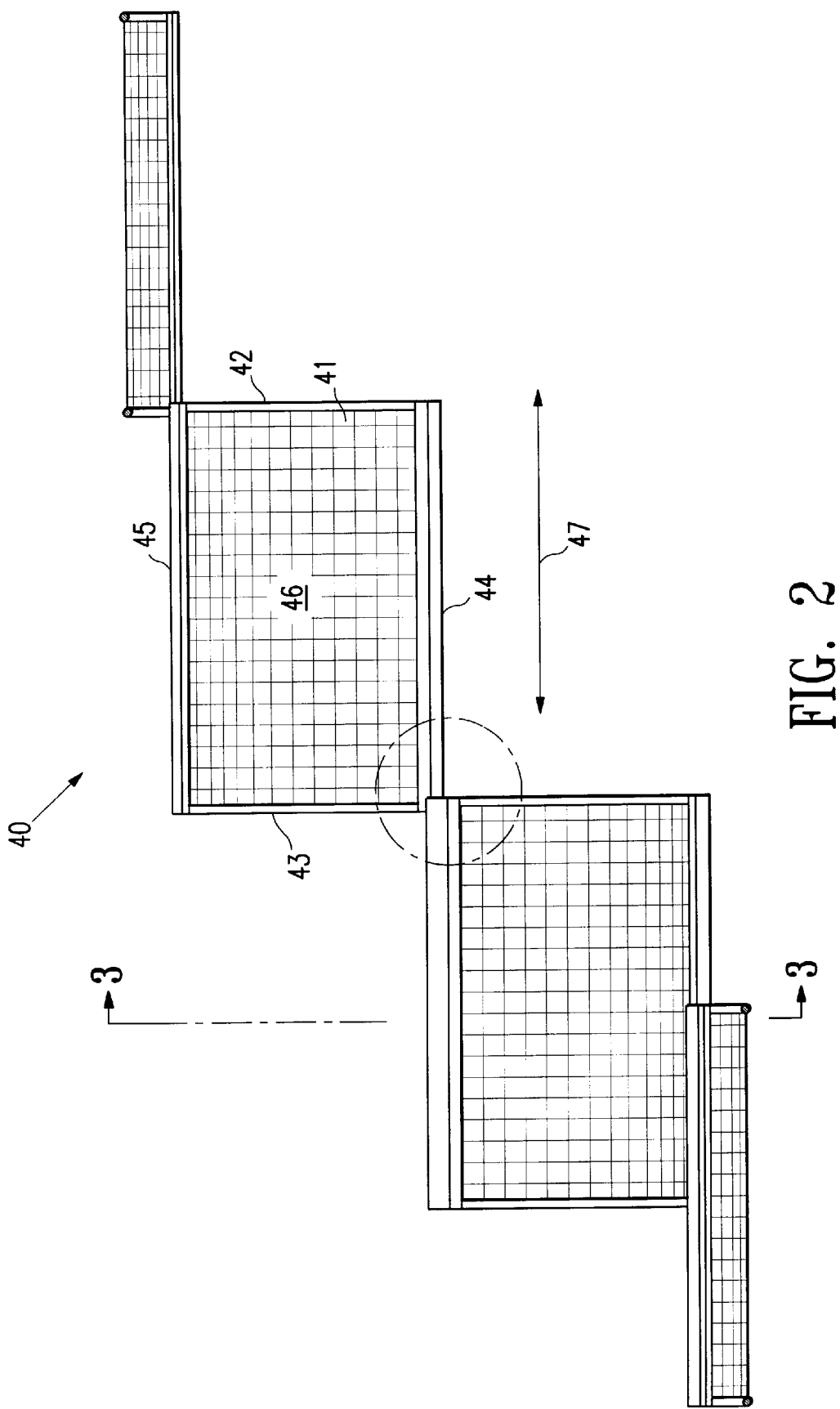
FIG. 2 shows a longitudinal cross section of an endovascular graft having features of the invention.

FIG. 2 shows a longitudinal cross sectional view of an endovascular graft 40 having features of the invention. The graft 40 has barrier sections 41 defined by a distal support member 42, a proximal support member 43, a male longitudinal member 44, a female longitudinal member 45, and a thin membrane 46. The thin membrane 46 is attached to the support members 42 and 43 and longitudinal members 44 and 45 by bonding with a suitable adhesive, but may also be attached by suturing, welding, crimping in a channel or other suitable methods. The male longitudinal member 44 is slidingly engaged or connected to the female longitudinal member 45 to allow relative axial or longitudinal movement or displacement, as indicated by the arrow 47, between the longitudinal members.

Figure 3:
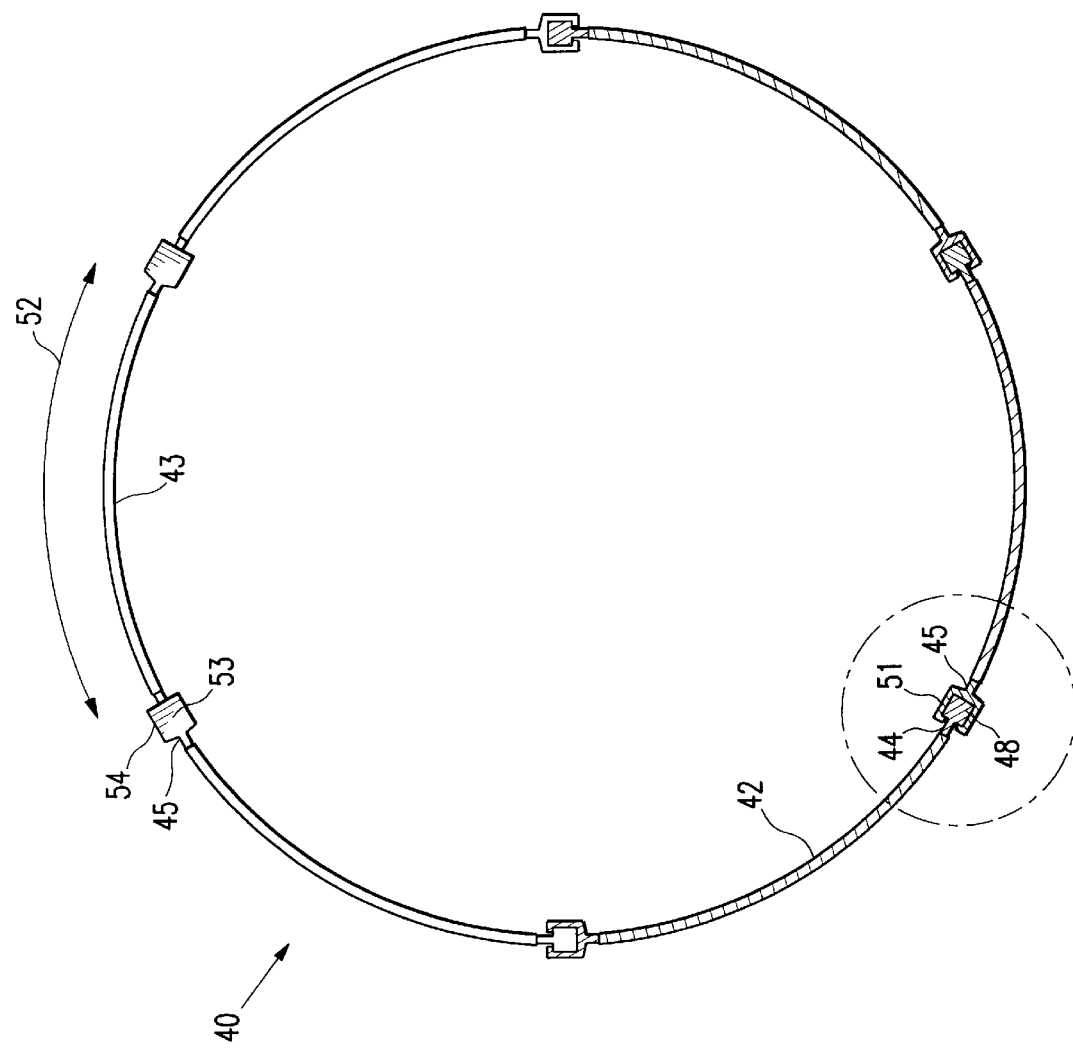
FIG. 3 shows a transverse cross sectional view of the endovascular graft of FIG. 2 taken at lines 3—3 of FIG. 2.

FIG. 3 is a transverse cross sectional view of the graft 40 of FIG. 2 taken at lines 3—3 of FIG. 2. Channel engager 48 of the male longitudinal member 44 is slidingly engaged or connected to channel 51 of the female longitudinal member 45. Proximal support member 43 and distal support member 42 are disposed between the male and female longitudinal members 44 and 45. The channel 51 and channel engager 48 are configured to allow relative axial movement between connected male and female longitudinal members 44 and 45 but restrict or limit relative circumferential movement, as indicated by the arrow 52, between the male and female longitudinal members 44 and 45. An end plate 53 is disposed at a proximal end 54 of the channel 51 of a female longitudinal member 45 to prevent egress of the channel engager 48 disposed in the channel in a proximal direction.

Figure 4:
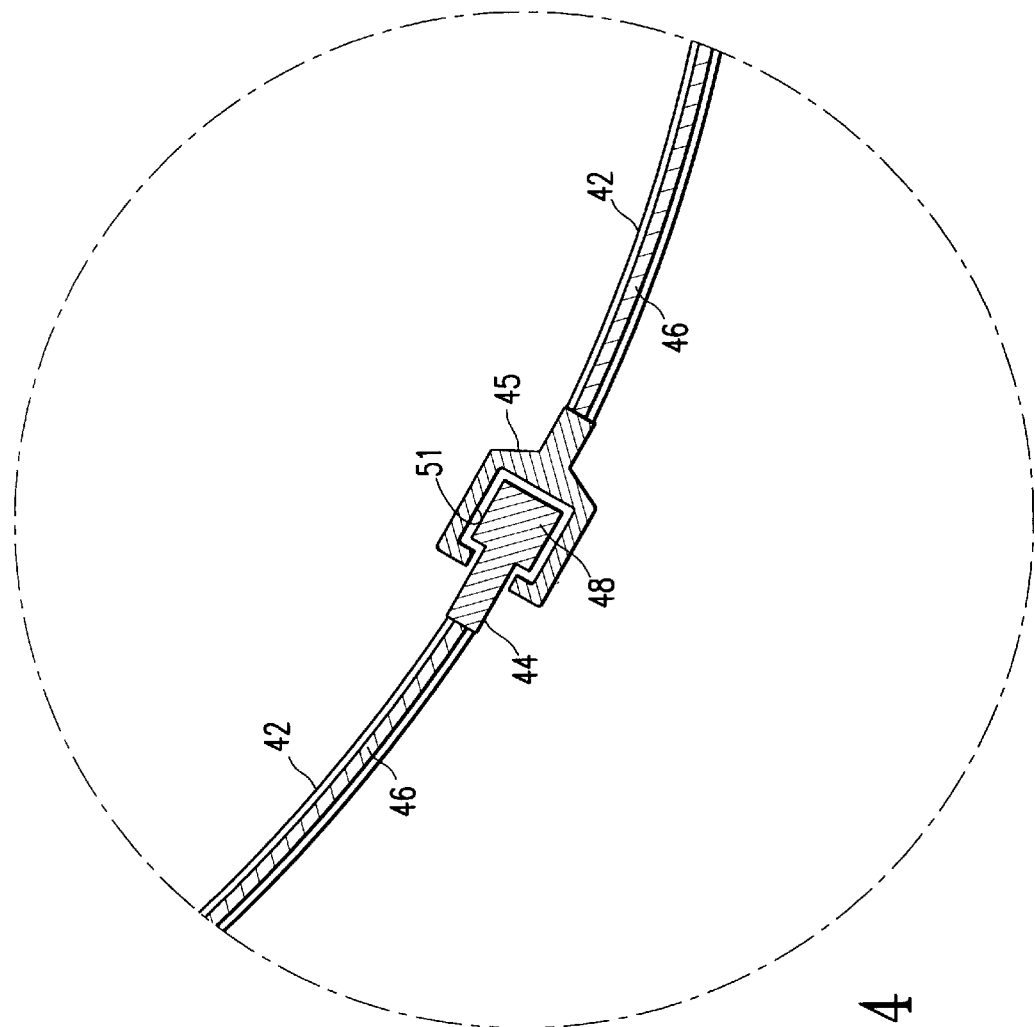
FIG. 4 is an enlarged isolation view of the encircled portion of FIG. 3.

FIG. 4 is an enlarged isolation view of the encircled portion of FIG. 3. A female longitudinal member 45 partially surrounds the channel engager 48 of a male longitudinal member 44 which has a square shape in order to limit relative rotational movement between the female and male longitudinal members. Extending circumferentially away from the male and female longitudinal members 44 and 45 are distal support members 42 in addition to thin membranes 46.

Figure 5:
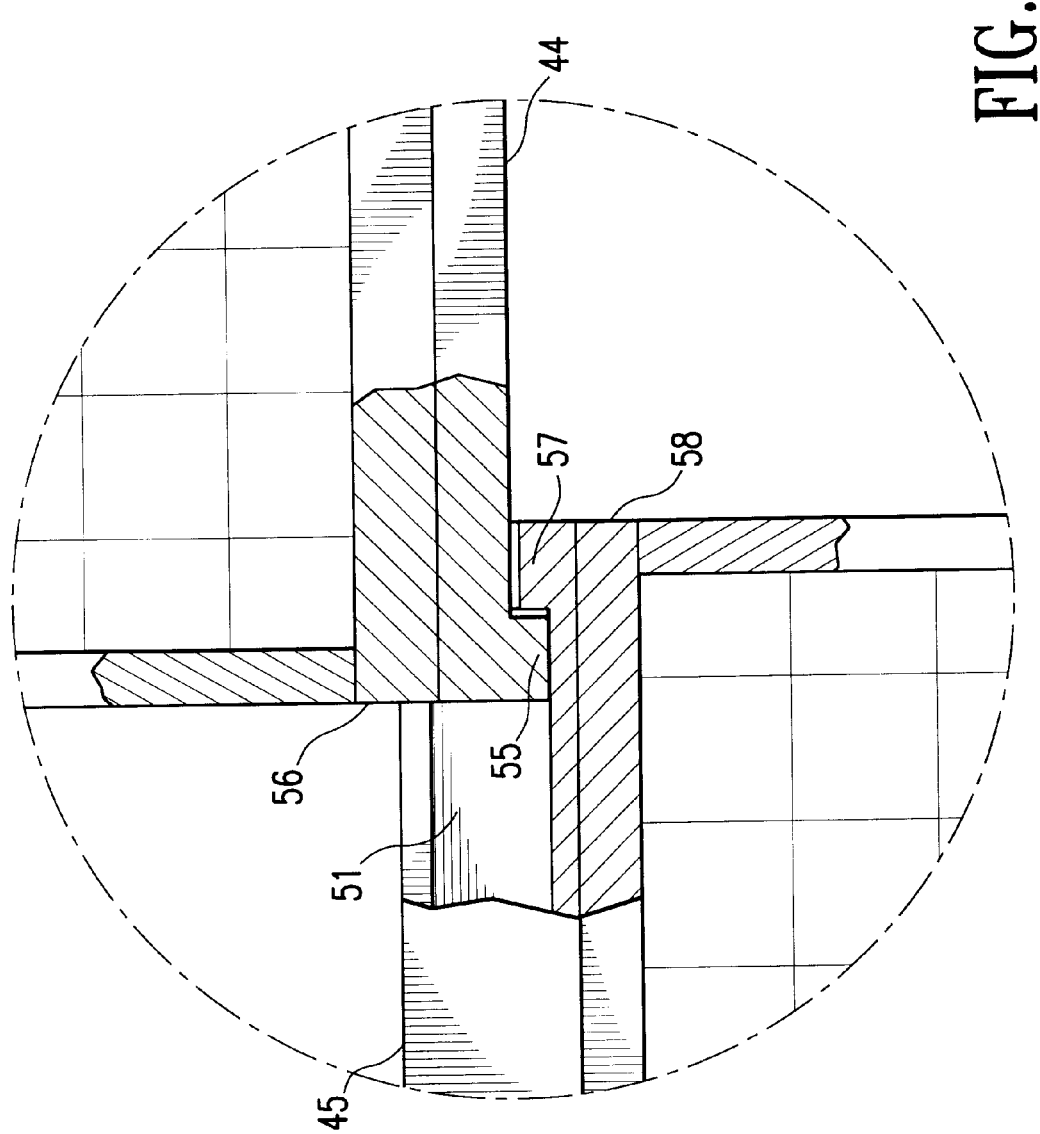
FIG. 5 is an enlarged isolation view in longitudinal cross section of the circled portion of the graft shown in FIG. 2.

FIG. 5 is an enlarged isolation view in longitudinal cross section of the circled portion of the graft shown in FIG. 2. The male longitudinal member 44 is engaged with the female longitudinal member 45. A first stop 55 is disposed on a proximal end 56 of the male longitudinal member 44 and a second stop 57 is disposed on a distal end 58 of the channel 51 of the female longitudinal member 45.

Figure 6:
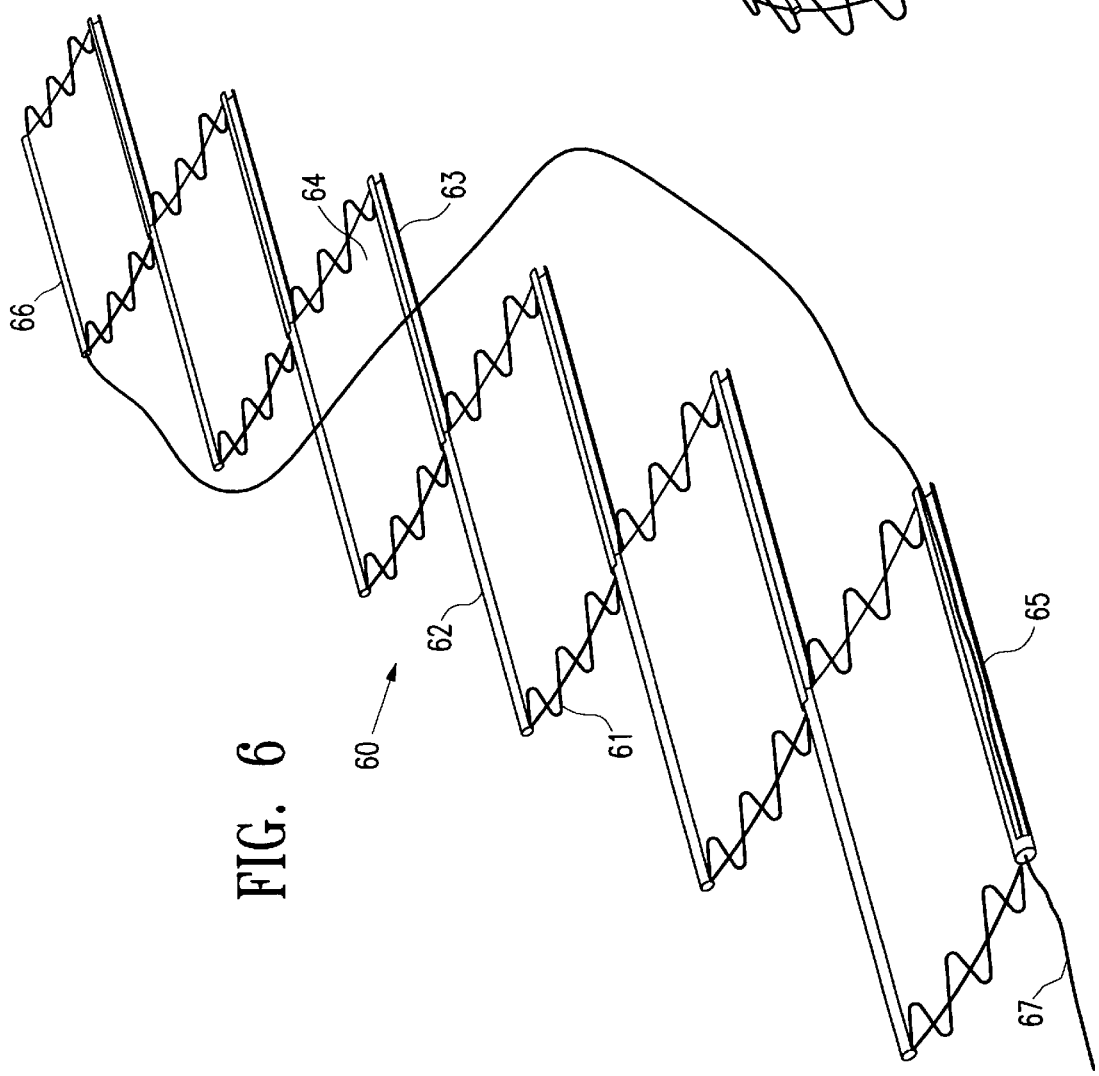
FIG. 6 shows a perspective view of an endovascular graft having features of the invention.
Figure 7:
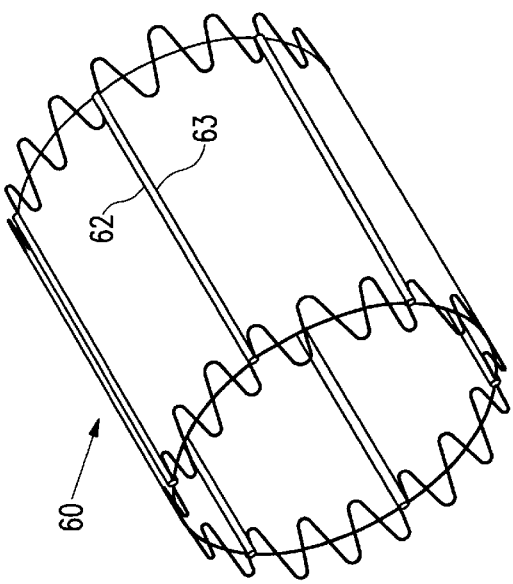
FIG. 7 shows the endovascular graft of FIG. 6 in a longitudinally and circumferentially contracted state.

FIG. 6 is a perspective view of an endovascular graft 60 having features of the invention, including an optional stent wire 61. Female longitudinal members 62 are slidingly engaged with adjacent male longitudinal members 63 of adjacent barrier members 64. A terminal male longitudinal member 65 and terminal female longitudinal member 66 are not slidingly engaged or connected, but are in mechanical communication via a closure wire 67 which runs through the terminal male longitudinal member 65 and terminal female longitudinal member 66 such that the members will be drawn together and ultimately slidingly engaged as the closure wire is shortened. FIG. 7 is a perspective view of the endovascular graft 60 of FIG. 6 in a closed axially compressed state wherein adjacent male and female longitudinal members 62 and 63 are substantially axially coextensive. In the closed state, the graft 60 can have an outside diameter or cross sectional dimension of about 10 to about 45 mm, preferably about 16 to about 28 mm.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An endovascular graft comprising at least two barrier sections which are formable into a substantially tubular structure with at least one barrier section having a first lateral edge and a second lateral edge slidably connected to at least one adjacent barrier section to allow axial movement of the at least one barrier section relative to the adjacent barrier section.

2. The endovascular graft of claim 1 wherein at least one barrier section further comprises a distal support member and a proximal support member and the distal support member, proximal support member, first lateral edge and second lateral edge of the barrier section defines a frame which surrounds an opening in the barrier section with the opening being covered by a thin membrane.

3. The endovascular graft of claim 2 wherein the thin membrane is comprised of a polymer.

4. The endovascular graft of claim 3 wherein the polymer of the thin membrane is ePTFE.

5. The endovascular graft of claim 2 wherein the frame is comprised at least in part of a pseudoelastic alloy.

6. The endovascular graft of claim 1 wherein the first lateral edge of at least one of the barrier sections comprises a female longitudinal member and a second lateral edge of an adjacent barrier section comprises a male longitudinal member which is at least partially slidably disposed within a channel of the female longitudinal member.

7. The endovascular graft of claim 6 wherein the male longitudinal member further comprises a channel engager with the channel of the female longitudinal member and the channel engager being configured to permit relative motion between the female longitudinal member and the male longitudinal member in an axial direction and restricted relative motion in a circumferential direction.

8. The endovascular graft of claim 7 wherein the channel of the female longitudinal member and the channel engager are configured to restrict relative rotation between the female longitudinal member and the male longitudinal member.

9. The endovascular graft of claim 7 wherein the channel of female longitudinal member and the channel engager of the male longitudinal member further comprise at least one stop configured to prevent disengagement of the longitudinal members.

10. A method of deploying an endovascular graft comprising a) providing an endovascular graft comprising at least two barrier sections which are formable into a substantially tubular structure with at least one barrier section having a first lateral edge and a second lateral edge with the lateral edges slidably connected to at least one adjacent barrier section to allow axial movement of the at least one barrier section relative to the adjacent barrier section;

b) stretching the endovascular graft in an axial direction by longitudinally displacing at least two of the barrier sections relative to each other;

c) loading the stretched endovascular graft into a delivery catheter;

d) positioning a distal end of the delivery catheter to a desired site within a patient's body channel; and e) deploying the graft from the distal end of the delivery catheter so as to axially compress at least some of the barrier sections of the graft relative to each other and form a substantially tubular member.

* * * * *